US006485715B1

(12) United States Patent
Smith et al.

(10) Patent No.: US 6,485,715 B1
(45) Date of Patent: Nov. 26, 2002

(54) STABLE PRESSURIZED ANTIPERSPIRANT COMPOSITIONS CONTAINING DIMETHYLETHER PROPELLANT AND A LOW POLARITY SOLVENT

(75) Inventors: Scott Edward Smith, Cincinnati, OH (US); David Frederick Swaile, Cincinnati, OH (US); Jennifer Elaine Hilvert, Cincinnati, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 0 days.

(21) Appl. No.: 09/864,012

(22) Filed: May 23, 2001

(51) Int. Cl.$^7$ .............................. A61K 7/32; A61K 7/00
(52) U.S. Cl. ..................... 424/65; 424/400; 424/401
(58) Field of Search ..................... 424/65, 401, 400

(56) References Cited

U.S. PATENT DOCUMENTS

| | | |
|---|---|---|
| 3,359,169 A | 12/1967 | Slater et al. |
| 3,405,153 A | 10/1968 | Jones et al. |
| 3,420,932 A | 1/1969 | Jones et al. |
| 3,472,928 A | 10/1969 | Virzi |
| 3,555,145 A | 1/1971 | Wetzel et al. |
| 3,555,146 A | 1/1971 | Jones et al. |
| 3,873,686 A | 3/1975 | Beekman |
| 3,876,758 A | 4/1975 | Beekman |
| 4,073,880 A | 2/1978 | Pader et al. |
| 4,083,954 A | 4/1978 | Tsuchiya et al. |
| 4,278,655 A | 7/1981 | Elmi |
| 5,318,778 A | 6/1994 | Schmucker et al. |
| 5,429,815 A | 7/1995 | Faryniarz et al. |
| 5,567,073 A | 10/1996 | de Laforcade et al. |
| 5,814,309 A | 9/1998 | Panitch |
| 5,961,963 A | 10/1999 | Temple |
| 5,968,489 A | * 10/1999 | Swaile et al. .................. 424/65 |
| 5,989,531 A | 11/1999 | Schamper et al. |
| 6,083,493 A | 7/2000 | Swaile |
| 6,096,297 A | 8/2000 | Jones et al. |

FOREIGN PATENT DOCUMENTS

| | | |
|---|---|---|
| EP | 0404532 A1 | 12/1990 |
| GB | 1285073 | 8/1972 |
| GB | 1300399 | 12/1972 |
| GB | 2113090 A | 8/1983 |
| JP | 57075912 | * 5/1982 |
| JP | 2898316 | * 5/1999 |
| WO | WO 96/18378 | 6/1996 |

* cited by examiner

*Primary Examiner*—Alton Pryor
(74) *Attorney, Agent, or Firm*—Jack L. Oney; Tara M. Rosnell; Steven W. Miller

(57) ABSTRACT

Disclosed are pressurized antiperspirant compositions comprising (a) a polyol solvent having at least 4 carbon atoms and a hydroxyl group on each of the $\alpha$ and $\beta$ carbon atoms of the polyol solvent; (b) solubilized antiperspirant active; (c) dimethylether; (d) a low polarity liquid having a solubility parameter of less than about 8.0, wherein the weight ratio of the dimethylether to low polarity solvent is from about 0.1 to about 2.8. It has been found that these compositions are especially useful in formulating clear or single-phase pressurized antiperspirant compositions that remain stable over prolonged periods and that can be formulated without ethanol or aqueous solvents.

22 Claims, No Drawings

STABLE PRESSURIZED ANTIPERSPIRANT COMPOSITIONS CONTAINING DIMETHYLETHER PROPELLANT AND A LOW POLARITY SOLVENT

TECHNICAL FIELD

The present invention relates to pressurized antiperspirant compositions comprising solubilized antiperspirant active, a dimethylether propellant, and a low polarity solvent. The compositions can be formulated as stable single phase or clear pressurized liquids without reliance upon ethanol, propylene glycol, or aqueous solvents.

BACKGROUND OF THE INVENTION

There are many different pressurized antiperspirant formulations known for use in controlling or inhibiting underarm perspiration and odor. Most of these formulations comprise an antiperspirant powder such as an aluminum salt, which is suspended in an anhydrous carrier and combined with a liquefied volatile propellant in a pressurized container. The formulation is then applied to the underarm as a pressurized spray which is, generated by the rapid boiling of the propellant upon dispensing from an atomizing valve in association with the pressurized container.

Although many consumers enjoy the convenience of an aerosol antiperspirant, many of these aerosols have highly undesirable application cosmetics. Activation of these aerosols often results in a dusty or powdery application, which then results in a heavy white residue on the applied areas of the skin. Moreover, the powdery residue on the skin tends to flake away or otherwise fall off relatively easily after application, especially when the applied surface comes in contact with clothing, thus resulting in an undesirable residue on the clothing itself and a loss or reduction of antiperspirant coverage on those areas of the skin from which the product has flaked away or otherwise fallen off.

To improve application cosmetics, some aerosol antiperspirants have been formulated with antiperspirant active dissolved or solubilized in a suitable aqueous or anhydrous carrier. Many of these formulations are also single phase systems without any dispersed or suspended solids, thus resulting in little or no visible residue on the applied areas that is attributable to the deposition of such dispersed or suspended solids on the skin. These single phase formulations often have a clear or translucent appearance, and apply neatly from an aerosolized spray without a dusty or powdery application. Many of these single phase aerosols, however, contain ethanol, or water to help solubilize the antiperspirant active to allow for the formulation of a stable, single-phase system. The aqueous formulations tend to feel wet during application and the ethanol formulations tend to irritate or sting the sensitive underarm area of the skin during and after application.

Single phase antiperspirant aerosols have also been described in the antiperspirant art in which single phase aerosols are formulated with dimethylether, solubilized antiperspirant active, and polyol solvents such as propylene glycol. These compositions contain dimethylether which allows for the formulation of a stable single-phase system, provided that the system also contains water, ethanol or relatively high propylene glycol concentrations to maintain the stability of the single phase system. Such compositions, however, tend to be unstable when formulated with substantive low polarity solvents, thus resulting in precipitation of antiperspirant active from solution or phase separation shortly after formulation, unless the compositions are modified to contain relatively high ethanol, water or propylene glycol concentrations. As noted throughout the antiperspirant art, high ethanol or propylene glycol concentrations can irritate or sting the sensitive underarm area of the skin and high water concentrations can result in an undesirably wet skin feel during and after application.

It has now been found that pressurized antiperspirant products can be formulated as single phase or clear products, without reliance upon high ethanol, propylene glycol, or water concentrations to solubilize and couple antiperspirant active with the various other ingredients to form a single phase or clear system. It has been found that single-phase, pressurized antiperspirants can be prepared without reliance upon such materials provided that it comprises an antiperspirant active solubilized in a polyol solvent having at least 4 carbon atoms and a hydroxyl group on each of the $\alpha$ and $\beta$ carbon atoms of the polyol solvent, wherein the solubilized active and selected polyol solvent are combined with a dimethylether propellant in combination with a low polarity solvent having a solubility parameter of less than about 8.0, wherein the weight ratio of the dimethylether to the low polarity solvent is from about 0.1 to about 3.0.

It has been found that the pressurized single-phase antiperspirant product will remain stable over prolonged periods, provided that the defined polyol solvent and dimethylether propellant are coupled with the low polarity solvent, and provided that the weight ratio of the dimethylether propellant to low polarity solvent is maintained within the range as defined here.

It has also been found that the above-described pressurized antiperspirant products remain stable over prolonged periods of time, and can be formulated as clear or single phase systems with low polarity solvents or materials. These low polarity solvents or materials can include materials such as volatile or non-volatile silicone fluids that provide additional benefits such as active substantivity, emolliency, improved skin feel during or after application, formulation flexibility, and similar other benefits. These low polarity solvents also include liquefied hydrocarbon propellants to provide a low cost option to more expensive propellant materials.

SUMMARY OF THE INVENTION

The present invention is directed to pressurized anhydrous antiperspirant compositions comprising: (a) a polyol solvent having at least 4 carbon atoms and a hydroxyl group on each of the $\alpha$ and $\beta$ carbon atoms of the polyol solvent; (b) solubilized antiperspirant active; (c) dimethylether; (d) a low polarity liquid having a solubility parameter of less than about 8.0, wherein the weight ratio of the dimethylether to low polarity solvent is from about 0.1 to about 3.0.

It has been found that these compositions are especially useful in formulating clear or single-phase pressurized antiperspirant compositions that remain stable over prolonged periods and that can be formulated without high concentrations of ethanol, propylene glycol or aqueous solvents. It has also been found that these compositions can be maintained as single phase or clear formulations, even when formulated with low polarity solvents such as silicone oils, liquefied hydrocarbon propellants, and other similar materials.

DETAILED DESCRIPTION OF THE INVENTION

The pressurized antiperspirant compositions of the present invention comprise a selected polyol solvent, a solubilized antiperspirant active, a dimethylether propellant, and a low polarity solvent in a defined weight ratio relative to the dimethylether propellant. These and other essential elements or limitations of the pressurized antiperspirant compositions of the present invention are described in detail hereinafter.

The term "anhydrous" as used herein, unless otherwise specified, refers to those compositions or materials containing less than about 5%, more preferably less than about 3%, even more preferably less than about 1%, even more preferably zero percent, by weight of free or added water.

The term "ambient conditions" as used herein refers to surrounding conditions at about one atmosphere of pressure, at about 50% relative humidity, and at about 25° C.

The term "pressurized antiperspirant" as used herein means any packaged antiperspirant composition that is pressurized from a gas or liquefied gas propellant to thus provide a means for pushing or moving the antiperspirant composition through an application device.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

The pressurized antiperspirant compositions of the present invention can comprise, consist of, or consist essentially of the essential elements and limitations of the invention described herein, as well as any additional or optional ingredients, components, or limitations described herein or otherwise useful in pressurized antiperspirant applications.

Liquid Polyols

The pressurized antiperspirant compositions of the present invention comprise selected liquid polyols for solubilizing or helping to solubilize the antiperspirant active material in the composition. The antiperspirant composition preferably comprises from about 1% to about 80%, more preferably from about 2% to about 60%, even more preferably from about 3% to about 20%, by weight of the selected liquid polyols.

The liquid polyols for use in the pressurized antiperspirant composition of the present invention are selected to have at least 4 carbon atoms and adjacent hydroxy-substituted carbon atoms at the α and β positions of the liquid polyol. Preferred liquid polyols for use in the compositions are those that conform to the formula:

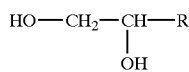

wherein R is an amide, ester, alkyl, ether or silicone-containing moiety, each moiety containing at least 2 carbon atoms. The R group is preferably an alkyl or ether group, more preferably an alkyl group having from about 2 to about 10 carbon atoms, more preferably from about 4 to about 6 carbon atoms. The liquid polyols preferably have either 2 or 3 hydroxyl groups in total.

The R group on the liquid polyol can therefore be substituted or unsubstituted, branched or straight or cyclic, saturated or unsaturated. Non limiting examples of suitable substituents include hydroxyl groups, amines, amides, esters, ethers, alkoxylate groups (e.g., ethoxylates, propoxylates, etc.) and so forth.

Non limiting examples of suitable liquid polyols for use in the pressurized compositions of the present invention include 1,2-butanediol; 1,2-pentanediol; 4-methyl-1,2-pentanediol; 2-methyl-1,2-pentanediol; 3,3-methyl-1,2-butanediol; 4-methyl-1,2-hexanediol; 1,2-heptanediol; 3-phenyl-1,2-propanediol; 1,2,6-hexanetriol; 1,2-hexandiol; 1,2,4-butanetriol; and combinations thereof. Other suitable liquid polyols include glycerol ethers such as glycerol isopropyl ether; glycerol propyl ether; glycerol ethyl ether; glycerol methyl ether; glycerol butyl ether; glycerol isopentyl ether; diglycerol isopropyl ether; diglycerol isobutyl ether; diglycerol; triglycerol; triglycerol isopropyl ether; and combinations thereof. Still other suitable liquid polyols include acetic acid glycerol ester; propanoic acid glycerol ester; butanoic acid glycerol ester; 3-methyl butanoic acid glycerol ester; and 3-trimethylsily-1,2-propane diol; silicone-containing 1,2-diols such as those described in U.S. Pat. No. 5,969,172 (Nye); and, combinations thereof.

These selected polyols are formulated into the antiperspirant composition alone or preferably in combination with one or more other anhydrous liquid carriers, examples of such other anhydrous liquid carriers include any known or otherwise effective carrier liquids suitable for topical application to the skin which are also compatible with the solubilized antiperspirant active and propellant components of the composition.

The pressurized antiperspirant compositions of the present invention are preferably anhydrous, but will typically contain at least small amounts of water associated with the antiperspirant active during formulation. In this context, the term anhydrous means the antiperspirant compositions of the present invention preferably contain less than 10%, more preferably less than 5%, even more preferably less than 3%, most preferably less than 1%, of water by weight of the composition.

Solubilized Antiperspirant Active

The pressurized antiperspirant compositions of the present invention comprise a solubilized antiperspirant active suitable for application to human skin. The concentration of antiperspirant active in the composition should be sufficient to provide the finished antiperspirant product with the desired perspiration wetness and odor control. The antiperspirant active is preferably solubilized by the liquid polyol component described hereinbefore.

Solubilized antiperspirant active concentrations in the pressurized antiperspirant compositions preferably range from about 0.1% to about 26%, more preferably from about 1% to about 20%, even more preferably from about 2% to about 10%, by weight of the composition. All such weight percentages are calculated on an anhydrous metal salt basis exclusive of water and any complexing or buffering agent such as glycine, glycine salts, or other complexing or buffering agent.

The solubilized antiperspirant active for use in the antiperspirant compositions of the present invention include any compound, composition or other material having antiperspirant activity. Preferred antiperspirant actives include astringent metallic salts, especially the inorganic and organic salts of aluminum, zirconium and zinc, as well as mixtures thereof. Particularly preferred are salts such as aluminum halides, aluminum chlorohydrate, aluminum hydroxyhalides, zirconyl oxyhalides, zirconyl hydroxyhalides, and mixtures thereof. Aluminum salts are most preferred for non-contact pressurized compositions.

Preferred aluminum salts for use in the antiperspirant compositions include those that conform to the formula:

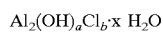

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "2/3 basic chlorhydroxide" wherein a =4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, and Gosling et al., issued Nov. 16, 1982, all of which are incorporated herein by reference. Mixtures of aluminum salts are described in British Patent Specification 1,347,950, Shin et al., published Feb. 27, 1974.

Zirconium salts for use in the antiperspirant compositions, especially in pressurized contact forms, include those which conform to the formula:

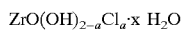

$$ZrO(OH)_{2-a}Cl_a \cdot x\, H_2O$$

wherein a is any number having a value of from 0 to about 2; x is from about 1 to about 7; and wherein a and x may both have non-integer values. Preferred zirconium salts are those complexes which additionally contain aluminum and glycine, commonly known as ZAG complexes. These ZAG complexes contain aluminum chlorhydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978.

Preferred antiperspirant actives for use in the compositions include aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum sulfate buffered, and combinations thereof.

Non limiting examples of solubilized antiperspirant active for use in the pressurized antiperspirant compositions of the present invention, and methods of making the solubilized active, are described in U.S. Pat. No. 6,149,897 (Swaile); U.S. Pat. No. 6,126,928 (Swaile); and U.S. Pat. No. 5,968,489 (Swaile et al.), which descriptions are incorporated herein by reference. Other non limiting examples of solubilized antiperspirant active and methods of making it are described in EP 0 404 533 (Smith et al.).

Propellant

The pressurized antiperspirant compositions of; the present invention comprise a dimethylether propellant in combination with a low polarity solvent as defined hereinafter, wherein the weight ratio of the dimethylether to the low polarity solvent ranges from about 0. 1 to 2.8, preferably from about 0.2 to about 1.0, more preferably from about 0.2 to about 0.5.

The propellant component of the pressurized antiperspirant compositions of the present invention may contain only dimethylether or a combination of dimethylether and any other known or otherwise suitable propellant for application to the skin, preferably a combination of dimethylether and a hydrocarbon propellant. The dimethylether or total propellant concentration in the pressurized antiperspirant compositions of the present invention ranges from about 5% to about 99%, more typically from about 15% to about 90%, even more preferably from about 30% to about 70%, by weight of the composition. The combination of dimethylether and hydrocarbon propellant preferably represents from about 50% to 100%, more preferably 100%, by weight of the total propellant concentration. Although less preferred, the compositions may comprise minor amounts of other propellants such as nitrous oxide, carbon dioxide, and halogenated hydrocarbons such as triclorofluoromethane, diclorodifluoromethane, diclorotetrafluoroethane trichlorotrifluoroethane, trichlorotetrafluoroethane, and monochlorodifluoromethane, and combinations thereof.

The hydrocarbon propellants suitable for use in the pressurized antiperspirant compositions include any hydrocarbon propellant known for or otherwise suitable for application to human skin, non limiting examples of which include propane, butane, pentane, isobutane, and combinations thereof. These hydrocarbon propellants are generally in the form of liquefied gases when formulated into the antiperspirant compositions, and are characterized for purposes of defining the compositions of the present invention as a low polarity solvent having a solubility parameter less than about 8.0, which low polarity solvents are described in greater detail hereinafter.

Low Polarity Solvent

The pressurized antiperspirant compositions of the present invention comprise a low polarity solvent in combination with the above-described dimethylether propellant, wherein the weight ratio of the dimethylether and low polarity solvent is selected within the defined range as described hereinbefore. The low polarity solvent can be any material that is liquid under ambient conditions or which is otherwise in liquid form within the pressurized composition described herein, and which has a solubility parameter of less than about 8.0, preferably from about 1 to about 6, more preferably from about 1 to about 4.

The low polarity solvent for use in the composition of the present invention is preferably a liquefied hydrocarbon propellant, non limiting examples of which include propane, butane, isopentane, pentane, isobutane, and combinations thereof. In this context, the liquefied hydrocarbon propellant acts as both a low polarity solvent and an additional propellant within the pressurized compositions. The hydrocarbon propellant as a low polarity solvent is preferably formulated in combination with the dimethylether propellant, wherein the weight ratio of dimethylether to hydrocarbon propellant in this preferred embodiment ranges from about 0.1 to 2.0, more preferably from about 0.1 to 1.0, even more preferably from about 0.2 to about 0.8.

Other low polarity solvents suitable for use in the pressurized antiperspirant compositions of the present invention include any silicone or silicone-containing material that is known or otherwise suitable for topical application to the skin, provided that the silicone or silicone-containing material is a liquid under ambient conditions or is otherwise in liquid form within the pressurized antiperspirant compositions of the present invention, and provided that the silicone or silicone-containing material has the requisite solubility parameter as defined herein. The silicone or silicone-containing material as a low polarity solvent for use in the pressurized antiperspirant compositions of the present invention can be a volatile or non volatile, cyclic or linear or branched chain, substituted or unsubstituted.

The concentration of the silicone liquid as a low polarity solvent in the composition preferably ranges from about 0.1% to about 50%, more preferably from about 1% to about 25%, more preferably from about 2% to about 15%, by weight of the pressurized antiperspirant composition.

Non limiting examples of suitable volatile silicones are described in Todd et al., "Volatile Silicone Fluids for Cosmetics", Cosmetics and Toiletries, 91:27–32 (1976), which descriptions are incorporated herein by reference. Preferred among these volatile silicones are the cyclic silicones having from about 3 to about 7, more preferably from about 4 to about 5, silicon atoms. Most preferably are those that conform to the formula:

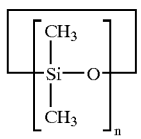

wherein n is from about 3 to about 7, preferably from about 4 to about 5, most preferably 5. These volatile cyclic silicones generally have a viscosity value of less than about 10 centistokes as measured at 25° C. Suitable volatile silicones for use herein include, but are not limited to, Cyclomethicone D-5 (commercially available from G. E. Silicones); DC 1184, Dow Corning 344, and Dow Corning 345 (commercially available from Dow Corning Corp.); GE 7207, GE 7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof. Cyclopentasiloxane is most preferred among the volatile silicone liquids.

Non limiting examples of non volatile silicone liquids for use in the pressurized antiperspirant compositions of the present invention include those which conform to either of the formulas:

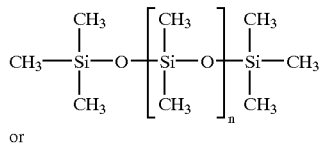

or

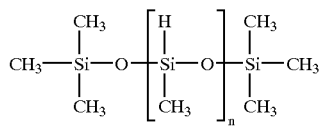

wherein n is greater than or equal to 1. These linear silicone materials will generally have viscosity values of from about 10 centistoke to about 100,000 centistoke, preferably less than about 500 centistoke, more preferably from about 20 centistoke to about 200 centistoke, even more preferably from about 20 centistoke to about 50 centistoke, as measured under ambient conditions. Non limiting examples of non-volatile, linear silicones suitable for use in the antiperspirant compositions include but are not limited to, Dow Corning 200, hexamethyldisiloxane, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G.E. Silicones); Velvasil and Viscasil (available from General Electric Co.); and Silicone L45, Silicone L530, Silicone L-531 (available from Union Carbide), and Siloxane F-221 and Silicone Fluid SWS-101 (available from SWS Silicones).

Other silicone liquids as low polarity solvents for use in the pressurized antiperspirant compositions of the present invention include modified or organofunctional silicone carriers such as polyalkylsiloxanes, polyalkyarylsiloxanes, cross-linked silicone elastomers, polyestersiloxanes, polyethersiloxane copolymers, polyfluorosiloxanes, polyaminosiloxanes, and combinations thereof. These modified silicone carriers are typically liquid under ambient conditions, and have a preferred viscosity of less than about 100,000 centistokes, more preferably less than about 500 centistokes, even more preferably from about 1 centistoke to about 50 centistokes, and most more preferably from about 1 centistoke to about 20 centistokes. These modified silicone carriers are generally known in the chemical arts, some examples of which are described in 1 *Cosmetics, Science and Technology* 27–104 (M. Balsam and E. Sagarin ed. 1972); U.S. Pat. No. 4,202,879, issued to Shelton on May 13, 1980; U.S. Pat. No. 5,069,897, issued to Orr on Dec. 3, 1991; which descriptions are incorporated herein by reference.

The pressurized antiperspirant compositions of the present invention may further comprise many other materials for use as the low polarity solvent, provided that such other materials have the defined solubility parameter and are formulated into the composition such that the weight ratio of the dimethylether to low polarity solvent remains within the ranges described herein. Such other materials include volatile and non volatile hydrocarbons in addition to or other than the hydrocarbon propellants described hereinbefore.

Optional Ingredients

The pressurized antiperspirant compositions of the present invention may further comprise other optional components which may modify the physical, chemical, cosmetic or aesthetic characteristics of the compositions or serve as additional "active" components when deposited on the skin. The compositions may also further comprise optional inert ingredients. Many such optional ingredients are known for use in deodorants, antiperspirants or other personal care compositions, and may also be used in the antiperspirant compositions herein, provided that such optional materials are compatible with the essential materials described herein, or do not otherwise unduly impair product performance.

Non limiting examples of optional ingredients include preservatives, deodorant antimicrobials, fragrances, deodorant perfumes, coloring agents or dyes, thickeners, pH modifiers, surfactants and other wash-off aids, co-solvents, emollients or residue masking liquids other than the silicone liquids described herein, pharmaceutical actives, vitamins, and combinations thereof. Preferred optional ingredients include dimethicone copolyols.

Although the pressurized antiperspirant compositions may further comprise any organic or silicone-containing liquid carrier other than the selected polyols and silicone liquids described herein, the compositions are preferably substantially free of ethanol, and also preferably substantially free of propylene glycol or dipropylene glycol. In this context, the term "substantially free" means that the pressurized antiperspirant compositions preferably contain less than 5%, more preferably less than 3%, even more preferably less than 1%, most preferably zero percent, by weight of any of these materials individually.

Product Form

The pressurized antiperspirant compositions of the present invention are preferably anhydrous formulations, and are also preferably clear or single-single phase liquids, although the present invention is not limited to clear or single-phase systems. These pressurized antiperspirant compositions are packaged in any known or otherwise suitable pressurized container for use in delivering the combination of materials described herein for any selected pressurized formulation. The pressurized antiperspirant compositions are also preferably free of any suspended or dispersed solids, e.g., insufficient solid concentrations to visibly reduce the clarity of the composition.

The pressurized antiperspirant composition may be packaged in conventional pressurized containers for use in contact or non-contact product forms. Non-contact products from pressurized containers are well known in the antiperspirant and personal care arts, non limiting examples of which are described in U.S. Pat. Nos. 3,082,917; 3,083,918; and 3,544,258, which descriptions are incorporated herein by reference. Pressurized contact antiperspirants are likewise known in the antiperspirant art, non limiting examples of which are described in U.S. Pat. No. 5,567,073 (de Laforcade et al.), which description is incorporated herein by reference.

The term "contact" or "contact product form" refers to any known or otherwise suitable pressurized package that comprises an applicator surface to which the antiperspirant composition is delivered under pressure from within the pressurized package, and from which the antiperspirant composition is then applied directly to the underarm area of the skin. In this context, the applicator surface directly contacts the underarm during application, thus delivering or depositing the antiperspirant composition to the underarm area of the skin.

The term "non-contact" or "non-contact product form" as used herein refers to pressurized packages from which the antiperspirant composition is delivered to the underarm through a product stream delivered under pressure from within the package to the skin. In this context, there is no direct contact between any surface of the pressurized package and the underarm.

Method of Manufacture

The pressurized antiperspirant compositions of the present invention may be prepared by any known or otherwise effective technique, suitable for making and formulating a clear or single phase pressurized antiperspirant formulation. These pressurized compositions are generally prepared by adding, individually or as a premix, all ingredients other than the dimethylether and any other selected propellant to a suitable container. The container is then sealed and residual air within the container is evacuated. The propellant is then added as a liquefied gas under appropriate pressures to the sealed container. Preferred compositions and methods of manufacture are described hereinafter in the following exemplified embodiments of the pressurized antiperspirant compositions of the present invention.

It has been found that the dimethylether propellant, when used in combination with a hydrocarbon or other similar propellant, is preferably added to the composition after the hydrocarbon or other similar propellant has been added. It has been found that this particular manufacturing sequence helps stabilize the composition during formulation, and thus minimize or eliminate any active precipitation during the manufacturing process. This particular manufacturing process is preferably applied to the pressurized antiperspirant compositions of the present invention, but can also be applied to any pressurized antiperspirant composition known or otherwise disclosed in the antiperspirant art that contains a solubilized antiperspirant active and a combination of dimethylether and other propellants such as liquefied hydrocarbon gases.

EXAMPLES

The following examples further describe and demonstrate specific embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, unless otherwise specified.

The compositions described below in Examples A–P are anhydrous, pressurized antiperspirant compositions that are single-phase systems having a clear or translucent appearance. Each of the compositions is packaged in a pressurized contact container, as well as a non-contact pressurized spray container. The products are applied to the underarm area of the skin to provide antiperspirant and deodorant efficacy. The products during and after application to the underarm result in little or no visible residue.

Each of the compositions described below (Examples A–P) is formulated by combining and mixing together in a glass bottle (suitable for pressurized packaging) all of the listed ingredients in each composition that are in liquid form under otherwise ambient conditions. The glass bottle is then sealed with a delivery valve and evacuated to between 14 and 25 inches of mercury. The propellant in each formulation is then added to the glass bottle under appropriate pressure using a burette filler. For those formulations containing more than one propellant material, the dimethylether is always added last. The resulting packaged composition is then heated in a water bath (150° F.) for 5 minutes to assure proper sealing of the valve. Each of the resulting compositions is a clear or single-phase pressurized antiperspirant composition that remains stable over prolonged periods of ambient storage without the use of solvents such as ethanol or aqueous solvents.

Each of the compositions described below (Examples A–P) is formulated with solubilized antiperspirant active solution. The solution is prepared by co-spray drying an initial antiperspirant active solution with a moderately polar solvent to form a spray dried active powder, and then dissolving the spray dried active powder in the desired 1,2-diol solvent with simple agitation over a few hours and no added heat, to thus form an antiperspirant active solution for formulation into the pressurized antiperspirant compositions exemplified herein. More specifically, the solubilized antiperspirant active for formulation into the pressurized antiperspirant compositions exemplified herein is prepared by making an aqueous mixture containing 40% by weight of either the aluminum chlorohydrate or aluminum zirconium chlorohydrate glycerin, 9% by weight of butylene glycol, and 2% by weight of polyethylene glycol 1000. The resulting aqueous mixture is then spray dried to provide a spray dried powder that contains about 65-75% by weight of anhydrous antiperspirant active and 20% by weight of the moderately polar solvent (solubility parameter of the moderately polar solvent being from about 9 to about 15). About 30 parts of the resulting spray-dried powder is then mixed with 70 parts of 1,2-hexanediol under ambient conditions, with simple agitation, and without added heat over approximately 2 hours to form the final antiperspirant active solution for formulation into the pressurized antiperspirant compositions exemplified herein.

TABLE 1

Anhydrous Pressurized Antiperspirant Products

| Ingredient | A | B | C | D | E | F | G | H |
|---|---|---|---|---|---|---|---|---|
| Dimethylether | 20 | 15 | 20 | 20 | 10 | 20 | 20 | 40 |
| Butane | 60 | 45 |  | 25 | 40 | 60 | 60 |  |
| Pentane |  |  | 60 |  |  |  |  |  |
| Isobutane |  |  |  | 30 |  |  |  |  |
| Propane |  |  |  | 3 |  |  |  |  |
| Aluminum chlorohydrate 15% solution in 1,2-hexanediol | 12 |  |  | 10 |  | 4 |  |  |
| Aluminum chlorohydrate 25% solution in isopropyl glycerol ether |  | 25 |  |  |  |  |  |  |
| Aluminum chlorohydrate 20% solution in butyl glycerol ether |  |  | 10 |  | 25 |  |  |  |
| Aluminum chlorohydrate 25% solution in 1,2-pentanediol |  |  |  |  |  |  | 13 | 20 |
| Dimethicone (10 cst) | 7 | 14 |  | 3 |  | 5 |  | 10 |
| Dimethicone copolyol |  |  | 4 | 3 | 10 |  | 6 | 5 |
| Cyclopentasiloxane |  |  | 5 | 3 | 14 | 10 |  | 25 |
| Fragrance | 1 | 1 | 1 | 1 | 1 | 1 | 1 |  |
| Weight ratio Dimethylether to low polarity solvent | 0.29 | 0.30 | 0.28 | 0.30 | 0.19 | 0.27 | 0.30 | 1.14 |

TABLE 2

Anhydrous Pressurized Antiperspirant Products

| Ingredient | I | J | K | L | M | N | O | P |
|---|---|---|---|---|---|---|---|---|
| Dimethylether | 30 | 15 | 20 | 20 | 50 | 40 | 30 | 20 |
| Butane |  |  | 19 |  |  |  |  | 20 |
| Isohexadecane |  |  |  |  | 25 |  |  |  |
| Mineral Oil |  |  |  |  |  | 30 |  |  |
| Aluminum chlorohydrate 20% solution in 1,2-hexanediol | 30 |  |  | 20 |  | 25 | 20 | 30 |
| Aluminum chlorohydrate 25% solution in isopropyl glycerol ether |  | 25 |  |  |  |  |  |  |
| Aluminum chlorohydrate 25% solution in butyl glycerol ether |  |  | 20 |  | 25 |  |  |  |
| Dimethicone (10 cst) |  | 14 | 20 | 10 |  |  |  | 10 |
| Dimethicone copolyol |  |  |  |  | 10 |  |  | 10 |
| Cyclopentasiloxane | 39 |  | 20 | 49 | 14 | 9 | 9 | 10 |
| Hexamethyl disiloxane |  | 45 |  |  |  |  |  |  |
| Fragrance | 1 | 1 | 1 | 1 | 1 | 1 | 1 |  |
| Weight ratio Dimethylether to low polarity solvent | 0.76 | 0.25 | 0.28 | 0.33 | 2.6 | 1.2 | 1.4 | 0.4 |

What is claimed is:

1. Liquid, single-phase, pressurized antiperspirant compositions comprising:
   (a) a polyol solvent having at least 4 carbon atoms and a hydroxyl group on each of the α and β carbon atoms of the polyol solvent;
   (b) solubilized antiperspirant active, wherein said active contains aluminum;
   (c) dimethylether; and
   (d) a low polarity solvent having a solubility parameter of less than about 8.0,
   wherein the weight ratio of the dimethylether to low polarity solvent is from about 0 1 to about 2.8,
   wherein said low polarity solvent is selected from the group consisting of volatile silicones, non-volatile silicones, polyalkyl siloxanes, polyalkylarylsiloxanes, polyether siloxane copolymers, liquefied hydrocarbon propellants, volatile liquid hydrocarbons, non-volatile liquid hydrocarbons, and combinations thereof.

2. The composition of claim 1 wherein the low polarity solvent comprises a hydrocarbon propellant.

3. The composition of claim 2 wherein the weight ratio of the dimethylether to hydrocarbon propellant is from about 0.1 to about 2.0.

4. The composition of claim 1 wherein the low polarity solvent comprises a silicone liquid.

5. The composition of claim 4 wherein the silicone liquid represents from about 0.1% to about 50% by weight of the composition.

6. The composition of claim 1 wherein the composition is anhydrous and contains less than 10% by weight of water.

7. The composition of claim 1 wherein the composition is anhydrous and contains less than 1% by weight of water.

8. The composition of claim 1 wherein the composition is visibly clear or translucent.

9. The composition of claim 1 wherein the composition is substantially free of ethanol.

10. The composition of claim 1 wherein the composition contains less 1% by weight of ethanol.

11. The composition of claim 1 wherein the composition is free of suspended or dispersed solids.

12. The composition of claim 1 wherein the antiperspirant active represents from about 0.1% to about 35% by weight of the composition and is selected from the group consisting of aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum sulfate buffered, and combinations thereof.

13. The composition of claim 1 wherein the selected polyol conforms to the formula:

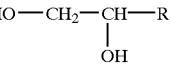

wherein R is an alkyl or ether group containing at least about 2 carbon atoms.

14. The composition of claim 13 wherein R is an alkyl group having from about 2 to about 6 carbon atoms.

15. The composition of claim 1 wherein the liquid polyol is selected from the group consisting of 1,2-butanediol; 1,2-pentanediol; 4-methyl-1,2-pentanediol; 2-methyl-1,2- pentanediol; 3,3-methyl-1,2-butanediol; 4-methyl-1,2-hexanediol; 1,2-heptanediol; 3-phenyl-1,2-propanediol; 1,2,6-hexanetriol; 1,2-hexandiol; 1,2,4-butanetriol; glycerol isopropyl ether; glycerol propyl ether; glycerol ethyl ether; glycerol methyl ether; glycerol butyl ether; glycerol isopentyl ether; diglycerol isopropyl ether; diglycerol isobutyl ether; diglycerol; triglycerol; triglycerol isopropyl ether; acetic acid glycerol ester; propanoic acid glycerol ester; butanoic acid glycerol ester; 3-methyl butanoic acid glycerol ester; and 3-trimethylsily-1,2-propane diol; and combinations thereof.

16. The composition of claim 15 wherein the liquid polyol comprises 1,2-hexanediol.

17. The composition of claim 15 wherein the liquid polyol comprises 1,2-pentanediol.

18. The composition of claim 1 wherein the composition is contained within a pressurized contact container.

19. The composition of claim 1 wherein the composition is contained within a pressurized non-contact container.

20. The composition of claim 1 wherein the low polarity solvent has a solubility parameter of from about 1 to about 4.

21. The composition of claim 1 wherein the weight ratio of the dimethylether to low polarity solvent is from about 0.2 to about 1.0.

22. The composition of claim 1 wherein the pressurized antiperspirant compositions comprise:
   (a) from about 3% to about 60% by weight of the polyol solvent;
   (b) from about 1% to about 10% by weight of the solubilized antiperspirant active; and
   (c) from about 5% to about 70% by weight of dimethylether;

and wherein the low polarity solvent comprises a hydrocarbon propellant selected from the group consisting of propane, pentane, butane, isobutane, isopentane, and combinations thereof.

* * * * *